(12) United States Patent
Lam

(10) Patent No.: US 9,844,431 B2
(45) Date of Patent: Dec. 19, 2017

(54) DENTAL FLOSS HOLDER

(71) Applicant: Wai Kwong Gordon Lam, Hong Kong (HK)

(72) Inventor: Wai Kwong Gordon Lam, Hong Kong (HK)

( * ) Notice: Subject to any disclaimer, the term of this patent is extended or adjusted under 35 U.S.C. 154(b) by 127 days.

(21) Appl. No.: 13/912,977

(22) Filed: Jun. 7, 2013

(65) Prior Publication Data

US 2013/0333720 A1    Dec. 19, 2013

(30) Foreign Application Priority Data

Jun. 8, 2012   (HK) .................................. 12105618.7

(51) Int. Cl.
    *A61C 15/04*      (2006.01)

(52) U.S. Cl.
    CPC .................................. *A61C 15/046* (2013.01)

(58) Field of Classification Search
    CPC ........................... A61C 15/046; A61C 15/048
    USPC .................................................. 132/321–329
    See application file for complete search history.

(56) References Cited

U.S. PATENT DOCUMENTS

| | | | | |
|---|---|---|---|---|
| 1,091,789 A * | 3/1914 | Andren | ................ | A61C 15/046 132/323 |
| 1,955,428 A * | 4/1934 | Ladwig | ......................... | 132/324 |
| 3,387,615 A * | 6/1968 | Mackew | ........................ | 132/323 |
| 3,939,853 A * | 2/1976 | Spanondis | ..................... | 132/323 |
| 4,434,806 A * | 3/1984 | Givens | .......................... | 132/323 |
| 4,440,184 A * | 4/1984 | Smith | ............................ | 132/323 |
| 4,738,271 A * | 4/1988 | Bianco | ................. | A61C 15/046 132/323 |
| 4,790,336 A * | 12/1988 | Kuo | .............................. | 132/325 |
| 5,232,002 A * | 8/1993 | McClallen | ..................... | 132/325 |
| 5,433,227 A * | 7/1995 | Chen | ............................. | 132/323 |
| 5,782,250 A * | 7/1998 | Harrah, Jr. | .................... | 132/327 |
| 6,164,294 A * | 12/2000 | Takabu | ......................... | 132/327 |
| 7,588,035 B2 * | 9/2009 | Ponzini | ........................ | 132/321 |
| 2009/0165814 A1 * | 7/2009 | Welt et al. | ..................... | 132/323 |

* cited by examiner

*Primary Examiner* — Todd E Manahan
*Assistant Examiner* — Brianne Kalach

(57) ABSTRACT

A dental floss holder comprising a holding portion, and a head portion disposed on the upper end thereof and bent obliquely upward from the holding portion. The head portion has first and second arm portions which symmetrically extend from the lower end of the head portion to both sides. Third and fourth arm portions symmetrically extend from the upper end of the head portion to both sides. First and second spaces for tensioning first and second segments of dental floss are formed between tail ends of the first and third arm portions, and the third and fourth arm portions, respectively. A third space for tensioning a third segment of dental floss is formed between tail ends of the fourth and second arm portions. The first and third segments of floss are parallel to the lengthwise direction of the holding portion, with the second segment of floss perpendicular thereto.

8 Claims, 4 Drawing Sheets

DENTAL FLOSS HOLDER

CROSS-REFERENCE TO RELATED APPLICATIONS

The present application claims priority to Hong Kong Patent Application No. 12105618.7 (Short-term Patent No. HK1165938), filed Jun. 8, 2012, the entirety of which is incorporated herein by reference

TECHNICAL FIELD

The invention relates to an oral hygiene appliance, and particularly to a dental floss holder.

BACKGROUND OF THE INVENTION

A dental floss holder is generally comprised of a holding portion, and a head portion used for tensioning a dental floss, the dental floss holders may be broadly divided into two types according to the relationship between the tensioned dental floss and the holding portion. As for the first type, the length direction of the holding portion of dental floss holders is generally parallel to the extension direction of tensioned dental flosses. The dental floss holders are relatively common and applicable for cleaning the teeth in the middle of the gums. But as for the teeth adjacent to both ends of the gums, such as wisdom teeth, due to the space limitation of the oral cavity, when the head portion of the dental floss holder is into the positions, the direction of the dental flosses may be deviated from the direction of interstices between teeth, and thus the cleaning work is relatively difficult. As for the second type, the length direction of the holding portion of a dental floss holder is perpendicular to the extension direction of its tensioned dental floss. This type of dental floss holders are applicable for cleaning the teeth adjacent to both ends of the gums but may be operationally inconvenient when used for cleaning the teeth adjacent to the middle of the gums. Because of the defects in design, both the two types of dental floss holders are not ergonomically designed, and are not conducive to fully and effectively clean the teeth.

SUMMARY OF THE INVENTION

The technical problem to be solved by the invention is to provide a dental floss holder that is ergonomically designed and capable of fully and effectively cleaning teeth, directed against the aforementioned defects of the dental floss holders in the existing art.

The technical solution adopted by the invention to solve the technical problem is that: forming a dental floss holder, which comprises a holding portion and a head portion, wherein the head portion is disposed on the upper end of the holding portion and bends towards an obliquely upward direction from the holding portion;

the head portion being provided with a first arm portion and a second arm portion which symmetrically extend from the lower end of the head portion to both sides, and a third at in portion and a fourth arm portion which symmetrically extend from the upper end of the head portion to both sides;

a first space used for tensioning a first segment of a dental floss being formed between the tail ends of the first arm portion and the third arm portion, a second space used for tensioning a second segment of the dental floss being formed between tail ends of the third arm portion and the fourth arm portion; a third space used for tensioning a third segment of the dental floss being formed between the tail ends of the fourth arm portion and the second arm portion, the first and the third segment of the dental floss are parallel to the lengthwise direction of the holding portion; and the second segment of the dental floss is perpendicular to the lengthwise direction of the holding portion.

In the dental floss holder provided by the invention, clamping grooves used for fixing dental flosses are respectively disposed at the tail ends of the first arm portion, the second arm portion, the third arm portion and the fourth arm portion.

In the dental floss holder provided by the invention, the head portion is provided with a threading hole for the dental floss to penetrate there through, and the threading hole is formed between the first arm portion and the second arm portion.

In the dental floss holder provided by the invention, winding grooves are formed on the lower end of the head portion.

In the dental floss holder provided by the invention, an indicating portion used for indicating the winding direction of the dental floss is disposed on the first arm portion.

In the dental floss holder provided by the invention, the indicating portion is raised or recessed.

In the dental floss holder provided by the invention, a plurality of non-slip projections are formed on the surface of the holding portion.

In the dental floss holder provided by the invention, a raised pressing portion is disposed on the holding portion adjacent to the head portion.

The dental floss holder provided by the invention has the following advantages: as the dental floss holder provided by the invention has three spaces for tensioning the dental floss and wherein the first and third segments of the dental floss respectively tensioned by the first space and the third segment of the dental floss are parallel to the lengthwise direction of the holding portion, for use of cleaning the teeth in the middle of the gums, and the second segment of the dental floss tensioned by the second space is perpendicular to the lengthwise direction of the holding portion, for use of cleaning the teeth adjacent to both ends of the gums, therefore the dental floss holder can fully and effectively cleaning the teeth.

BRIEF DESCRIPTION OF THE DRAWINGS the invention will be described in detail with embodiments in conjunction with the drawings. In the drawings.

DETAILED DESCRIPTION OF THE PREFERRED EMBODIMENTS

For clearer understanding of the technical characteristics, objectives and advantages of the invention, the preferred embodiments of the invention will be described in detail in conjunction with the drawings.

Figure 1:
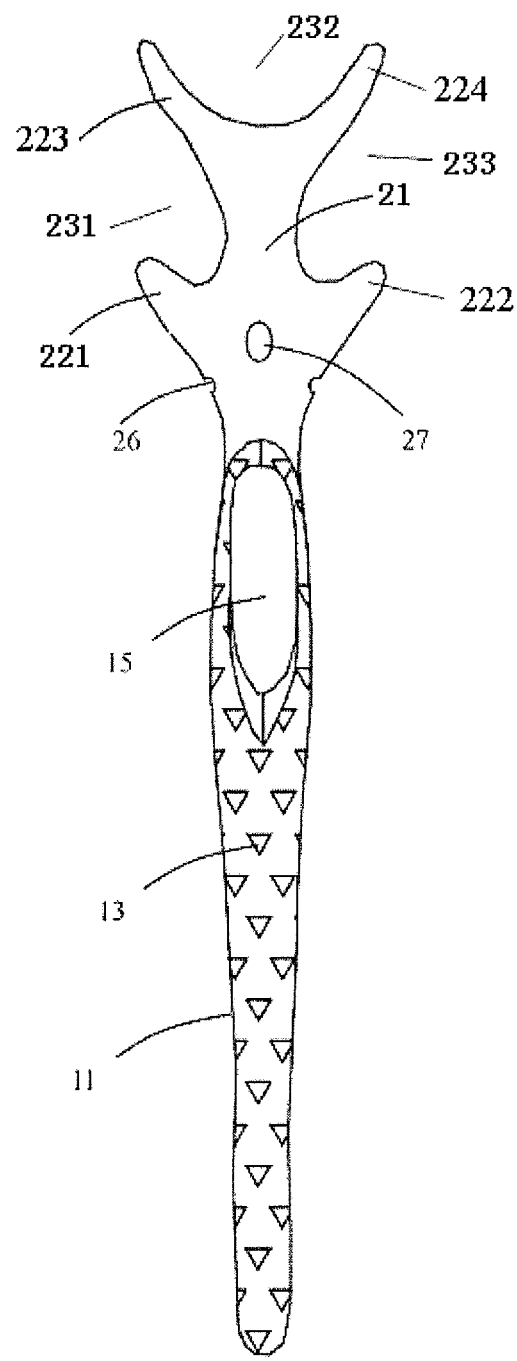
FIG. 1 is a front view of the first embodiment of a dental floss holder provided by the invention.
Figure 2:
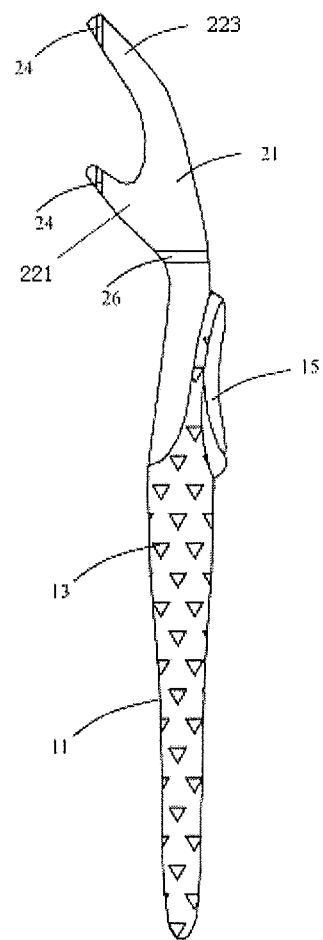
FIG. 2 is a side view of the first embodiment of the dental floss holder provided by the invention.
Figure 3:
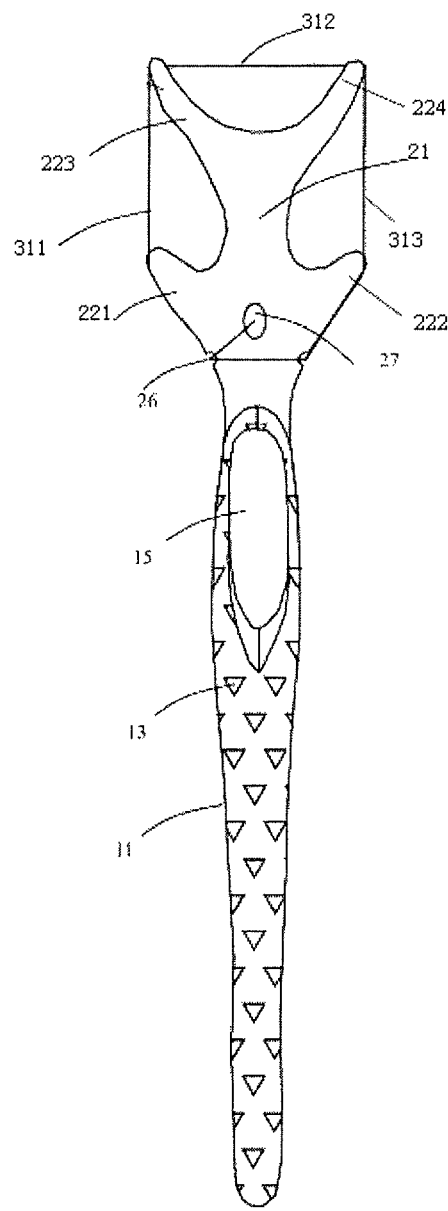
FIG. 3 is a schematic diagram of the first embodiment of the dental floss holder provided by the invention when a dental floss is mounted.

As illustrated in FIGS. 1 to 3, which are the schematic diagrams of the first embodiment of a dental floss holder provided by the invention, in an embodiment a three-directional dental floss holder is provided, which comprises a holding portion 11 and a head portion 21, wherein the head portion 21 is disposed on the upper end of the holding portion 11, and bends towards an obliquely upward direction from the holding portion 11. The head portion 21 is provided with extended arm portions used for mounting a dental floss. The curved shape of the head portion 21 is ergonomically designed, so that the dental floss can be used for maximum direct contact with teeth. Moreover, the design of appropriate average size is provided so as to ensure the comfort and safety of use.

In order to more fully clean teeth, in the dental floss holder provided by the invention, the head portion 21 has four arm portions. More specifically, the head portion 21 is provided with a first arm portion 221 and a second arm portion 222 which symmetrically extend from the lower end of the head portion 21 to both sides, and a third arm portion 223 and a fourth arm portion 224 which symmetrically extend from the upper end of the head portion 21 to both sides. A first space 231 used for tensioning a first segment 311 of the dental floss is formed between the tail ends of the first arm portion 221 and the third arm portion 223, a second space 232 used for tensioning a second segment 312 of the dental floss is formed between the tail ends of the third arm portion 223 and the fourth arm portion 224, a third space 233 used for tensioning a third segment 313 of the dental floss is formed between the tail ends of the fourth arm portion 224 and the second arm portion 222. The first segment 311 and the third segment 313 of the dental floss are parallel to the lengthwise direction of the holding portion 11, and the second segment 312 of the dental floss is perpendicular to the lengthwise direction of the holding portion 11. Moreover, the first segment 311, the second segment 312 and the third segment 313 of the dental floss are parts of the same dental floss, i.e., formed by the same dental floss winding on the dental floss holder. As the first segment 311 and the third segment 313 of the dental floss respectively tensioned by the first space 231 and the third space 233 are parallel to the lengthwise direction of the holding portion 11, the segments can be used for cleaning the teeth in the middle of the gums. As the second segment 312 of the dental floss tensioned by the second space 232 is perpendicular to the lengthwise direction of the holding portion 11, the segment can be used for cleaning the teeth adjacent to both ends of the gums. Resulting from above, the dental floss holder can fully and effectively clean teeth. The three-directional dental floss holder provided by the embodiment is ergonomically designed in structure, can be used in different directions and angles, and is conducive to eliminate dental plaque and tartar between teeth to the greatest degree.

In the embodiment, for the convenience of fixing the dental floss, clamping grooves 24 used for fixing the dental floss are respectively formed at the tail ends of the first arm portion 221, the second arm portion 222, the third arm portion 223 and the fourth arm portion 224. The dental floss may be clamped into the clamping grooves 24, so that the dental floss holder has the function of positioning and fixing the dental floss during tensioning. In addition, the head portion 21 of the dental floss holder is provided with a threading hole 27 formed between the first arm portion 221 and the second arm portion 222 for the dental floss to penetrate through. Moreover, winding grooves 26 are formed on the lower end of the head portion 21 of the dental floss holder. During threading, at first one only needs to gently pull the dental floss from the threading hole 27 arranged in the middle to one of the winding grooves 26, wind and pull it to the winding groove 26 on the other side, and then wind it repeatedly to and for around an axis of the holding portion 11, and sleeve it on the end portions of the four arm portions to form a solid three-directional dental floss, and finally pull the dental floss to one of the winding groove 26 and wind and pull it to the winding groove 26 on the other side, whereby firmed overall structure is formed. The design ensures that the dental floss has sufficient tension to allow a user to remove the dental plaque and tartar between his/her teeth, without using fingers to adjust the dental floss. Due to the above structure, the dental floss holder has the advantages of higher structural strength and larger cleaning area.

In the embodiment, the holding portion 11 is made of rigid plastics, and provided with a plurality of non-slip projections 13, which are small lugs, formed on the surface thereof for enhancing comfort and achieving a non-slip function. Moreover, a raised pressing portion 15 is disposed on the holding portion 11 adjacent to the head portion 21, through which a user can use the dental floss holder for pressing, and thus the user's experience can be improved.

Figure 4:
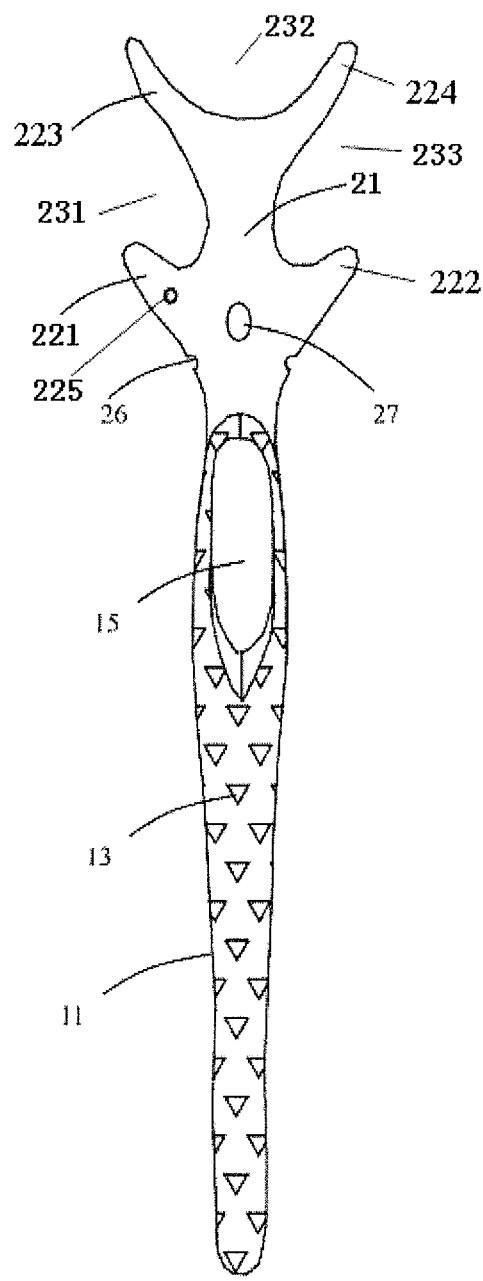
FIG. 4 is a schematic diagram of the second embodiment of the dental floss holder provided by the invention.

As illustrated in FIG. 4, which is a schematic diagram of a second embodiment of the dental floss holder provided by the invention, the structure of the dental floss holder of the embodiment is basically the same with that of the dental floss holder of the first embodiment. The differences are as follows: an indicating portion 225 used for indicating the winding direction of the dental floss is disposed on the first arm portion 221 and may be raised or recessed or may be a point of which the color is different from the surrounding color. The indicating portion may be used for indicating the starting point and the initial direction of winding of the dental floss, so that the dental floss can be conveniently winded on the dental floss holder.

As the dental floss holder provided by the invention has three spaces for tensioning the dental floss and wherein the first segment and the third segment of the dental floss respectively tensioned by the first space and the third space are parallel to the lengthwise direction of the holding portion, the dental floss holder can be used for cleaning the teeth in the middle of the gums. Furthermore, as the second segment of the dental floss tensioned by the second space is perpendicular to the lengthwise direction of the holding portion, the dental floss holder can be used for cleaning the teeth adjacent to both ends of the gums. Resulting from above, the dental floss holder can fully and effectively cleaning teeth.

The invention have been described in detail with embodiments in conjunction with the drawings, the invention should not be limited to the above embodiments. The preferred embodiments are only illustrative but not limitative. Many modifications can still be made by those skilled in the art on the basis of the invention without departing from the objective of the invention and the scope of protection as defined by the claims, and these modifications shall all fall within the scope of protection of the invention.

What is claimed is:

1. A dental floss holder for holding only three exposed teeth-cleaning segments of a dental floss, the dental floss holder comprising a holding portion and a head portion, wherein said head portion is disposed on an upper end of said holding portion and bends towards an obliquely upward direction from said holding portion, the holding portion defining a longitudinal axis extending in a longitudinal direction; said head portion being provided with a first arm portion and a second arm portion that symmetrically extend from a lower end of said head portion to both sides, and a third arm portion and a fourth arm portion that symmetrically extend from an upper end of the said head portion to both sides, each arm portion has a tail end;

a first space for tensioning a first exposed segment of the dental floss being formed between the tail ends of the first arm portion and said third arm portion, a second space for tensioning a second exposed segment of the dental floss being formed between the tail ends of said third arm portion and said fourth arm portion, a third space for tensioning a third exposed segment of the dental floss being formed between the tail ends of said fourth arm portion and said second aim portion, said first exposed segment and said third exposed. segment of the dental floss are parallel to the longitudinal direction of the holding portion, said second exposed segment of the dental floss is perpendicular to the longitudinal direction of said holding portion, wherein the first, second, and third exposed segments are the only three exposed segments of the dental floss for cleaning teeth;

four clamping grooves for fixing the dental floss being respectively disposed at the tail ends of said first arm portion, said second arm portion, said third aim portion and said fourtharm portion, wherein the four clamping grooves and the first, second and third exposedsegments of the dental floss are all lying on a plane parallel to and offset from the longitudinal axis of the holding portion; said head portion being provided with a threading hole for the dental floss to penetrate through, said threading hole being formed transversely through said head portion between said first arm portion and said second ann portion;

two winding grooves being formed on the lower end of said head portion at two opposite sides thereof respectively, said two winding grooves lying on a plane perpendicular to the longitudinal axis so that the dental floss is wound around the lower end of the head portion;

an indicating portion for indicating winding direction of said dental floss being disposed on said first arm portion, the indicating portion being a raised or recessed dot;

a plurality of non-slip projections being formed on a surface of said holding portion, and a raised pressing portion being disposed on said holding portion adjacent to said head portion.

2. A dental floss holder for holding only three exposed teeth-cleaning segments of a dental floss, the dental floss holder comprising a holding portion and a head portion, wherein said head portion is disposed on an upper end of said holding portion and bends towards an obliquely upward direction from said holding portion, the holding portion defining a longitudinal axis extending in a longitudinal direction; said head portion being provided with a first arm portion and a second arm portion that symmetrically extend from a lower end of said head portion to both sides, and a third ann portion and a fourth arm portion that symmetrically extend from an upper end of said head portion to both sides, each arm portion has a tail end;

a first space for tensioning a first exposed segment of the dental floss is formed between the tail ends of said first arm portion and said third arm portion, a second space for tensioning a second exposed sement of the dental floss being formed between the tail ends of said third ann portion and said fourth arm portion, a third space for tensioning a third exposed segment of the dental floss being formed between the tail ends of said fourth arm portion and said second arm portion, said first exposed segment and said third exposed segment of the dental floss are parallel to the longitudinal direction of said holding portion, and said second exposed segment of the dental floss is perpendicular to the longitudinal direction of said holding portion, wherein the first, second, and third exposed segments are the only three exposed segments of the dental floss for cleaning teeth;

wherein four clamping grooves for fixing the dental floss are respectively disposed at the tail ends of the first am portion, the second am portion, the third arm portion and the fourth arm portion; the four clamping grooves and the first, second and third exposed segments of the dental floss are all lying on a plane parallel to and offset from the longitudinal axis of the holding portion.

3. The dental floss holder according to claim 2, wherein said head portion is provided with a threading hole for said dental floss to penetrate through, and said threading hole is formed transversely through the head portion between said first arm portion and said second arm portion.

4. The dental floss holder according to claim 2, wherein two winding grooves are formed on the lower end of said head portion at two opposite sides thereof respectively, said two winding grooves lying on a plane perpendicular to the longitudinal axis so that the dental floss is wound around the lower end of the head portion.

5. The dental floss holder according to claim 2, wherein an indicating portion for indicating winding direction of said dental floss is disposed on said first arm portion.

6. The dental floss holder according to claim 5, wherein said indicating portion is a raised or recessed dot.

7. The dental floss holder according to claim 2, wherein a plurality of non-slip projections are formed on a surface of said holding portion.

8. The dental floss holder according to claim 2, wherein a raised pressing portion is disposed on said holding portion adjacent to said head portion.

* * * * *